US00PP10173P

United States Patent [19]

Meilland

[11] Patent Number: Plant 10,173

[45] Date of Patent: Jan. 6, 1998

[54] HYBRID TEA ROSE PLANT NAMED 'MEIYACOM'

[75] Inventor: Alain A. Meilland, Antibes, France

[73] Assignee: The Conard-Pyle Company, West Grove, Pa.

[21] Appl. No.: 663,790

[22] Filed: Jun. 14, 1996

[51] Int. Cl.[6] ..... A01H 5/00

[52] U.S. Cl. ..... Plt./18

[58] Field of Search ..... Plt./18, 11, 16

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive long-lasting blossoms that are light Orient Pink with some light green coloration. The plant exhibits an erect growth habit and strong vegetation. The floral buds are large and the blossoms possess a large number of petals. Such blossoms are borne on very long and strong stems and tend to open in a configuration resembling that of a garden rose. The new variety exhibits very good disease resistance and is particularly well suited for cut flower production under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Meitalmin' variety (non-patented in the United States). The male parent (i.e., the pollen parent) was the product of the cross of the 'Meidiaplou' variety (U.S. Plant Pat. No. 7,624) and the 'Delpoid' variety (non-patented in the United States). The parentage of the new variety can be summarized as follows:

'Meitalmin'×('Meidiaplou'×'Delpoid').

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance long-lasting attractive blossoms that are light Orient Pink with some light green coloration,
(b) exhibits an erect growth habit,
(c) exhibits blossoms possessing a slight fragrance,
(d) is well suited for cut flower production under greenhouse growing conditions, and
(e) exhibits very good disease resistance.

The floral buds are large and the blossoms possess a large number of petals. Such blossoms are borne on very long and strong stems and tend to open in a configuration resembling that of a garden rose.

The new variety well meets the needs of the horticultural industry and is particularly well suited for the commercial producton of cut flowers while growing indoors.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meiyacom' variety, and is being marketed under the CLAUDIA trademark.

BRIEF DESCRIPTION OF THE PHOTOGRAPH

The accompanying photograph shows a nearly true as it is reasonably possible to make the same, in a color illustration of this character, typical specimens of the plant parts of the new variety. The rose plants of the new variety were two years of age and were observed during September while budded on *Rosa indica* understock and growing in greenhouses at Le Cannet des Maures, Var. France.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface; and FIG. 15 — illustrates a specimen of a leaf with five leaflets — plan view — under surface.

DETAILED DESCRIPTION

Figures 1, 2, 3, 4, 5, 6, 7, 8, 9, 10, 11, 12, 13, 14, 15:
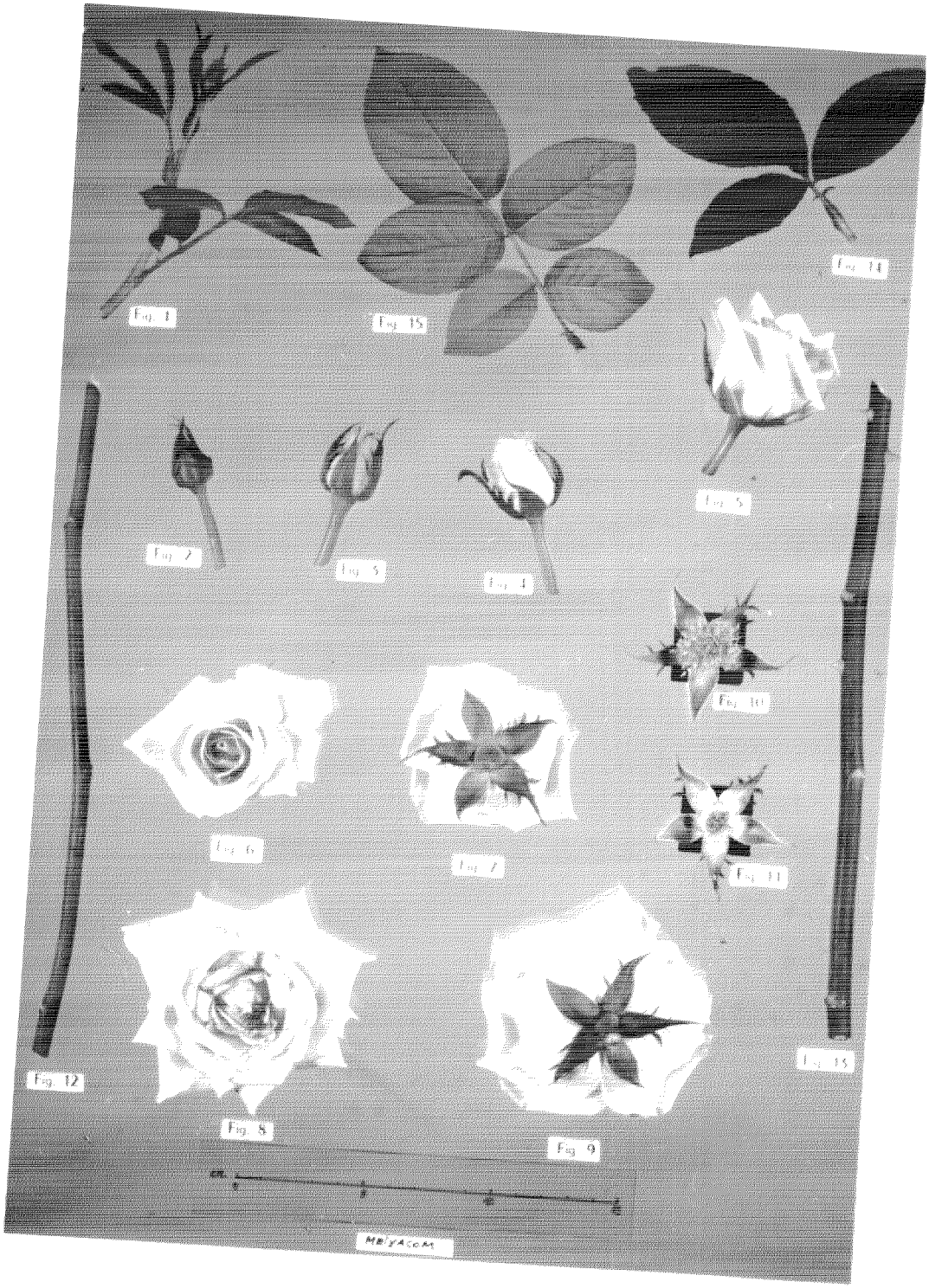

The chart used in the identification of the colors is that of The Royal Horticultural Society (R.H.S. Colour Chart). The description is based on the observation during September of two-year-old plants while budded on *Rosa indica* understock and growing in greenhouses at Le Cannet des Maures, Var, France. The coloration in common terms precedes reference to the chart.

Class: Hybrid Tea.

Plant:

*Height.*—Approximately 60 to 80 cm. on average at the end of the growing season.

*Habit.*—Erect.

Branches:

*Color.*—Young stems: medium green, Green Group 143B. Adult wood: medium green, Green Group 137A.

*Thorns.*—Size: medium. Quantity: few, and often none on young stems. Color: Yellow-Green Group 144A on young stems and Greyed-Orange Group 163A on adult wood.

Leaves:

*Stipules.*—Adnate, pectinate, very large and linear.

*Petioles.*—Upper surface: striped reddish brown on young foliage and medium green on adult foliage, and more or less glandular. Under surface: medium green and commonly with some small thorns. Color: near Yellow-Green Group 144A.

*Leaflets.*—Number: commonly 3, 5 and 7 (most often). Shape: oval. Serration: single and regular (as illustrated). Texture: consistent. Size: large. General appearance: dense, and semi-glossy. Color (young foliage): upper surface: medium green, Green Group 137B, and more or less tinted with reddish coloration. under surface: light green, Green Group 143C and more or less tinted with reddish coloration. Color (adult foliage): upper surface: medium green, Green Group 137A. under surface: light green, Greyed-Green Group 191A.

Inflorescence:

*Number of flowers.*—Usually one flower per stem and sometimes up to three flowers per stem.

*Peduncle.*—Light green in coloration and more or less glandular. The length is approximately 6 to 8 cm. on average.

*Sepals.*—Upper surface: tomentose, and near Green Group 137C. in coloration. Under surface: Green Group 137C. in coloration and commonly with appendiculate edges of medium length (as illustrated).

*Stem length.*—Commonly approximately 60 to 80 cm. on average when grown under greenhouse conditions.

*Buds.* —Shape: ovoid. Length: approximately 3 cm. on average. Size: large. Color upon opening: upper surface: light Orient Pink, Red Group 36D, and edged with light green, Yellow-Green Group 144C. under surface: light Empire Rose, Red Group 50D, and more or less edged and suffused with light green, Yellow-Green Group 144C.

*Flower.*—Shape: cup-shaped (as illustrated). Diameter: approximately 10 cm. on average. Color (when opening begins): upper surface: light Orient Pink, Red Group 36D and more or less edged and suffused with Carmine Rose, Red Group 52D. under surface: light Empire Rose, Red Group 50D, and more or less edged and suffused with light green, Yellow-Green Group 144C. Color (when blooming): upper surface: light Orient Pink, Red Group 36D and more or less edged and suffused with Carmine Rose, Red Group 52D. under surface: light Empire Rose, Red Group 50D, and more or less edged and suffused with light green, Yellow-Green Group 144C. Color (at end of opening): upper surface: light Orient Pink, Red Group 36D and more or less edged and suffused with Carmine Rose, Red Group 52D. under surface: light Empire Rose, Red Group 50D, and more or less edged and suffused with light green, Yellow-Green Group 144C. The coloration tends to whiten somewhat on the external petals. Fragrance: slight. Lasting quality: very long. The blossoms commonly last approximately 8 to 10 days when cut and placed in a vase. The blossom life is influenced by the environmental conditions that are encountered. Petal drop: good. Petal shape: rounded with reflexed edges. Petal number: commonly approximately 30 to 35 on average. Stamen number: approximately 55 on average. Anthers: normal ochre in coloration. Filaments: strawlike in coloration. Distils: approximately 105 on average. Stigmas: normal. Styles: dark fuchsine in coloration, and more or less twisted and tomentose. Receptacle: medium green in coloration, smooth, and in longitudinal section in the shape of a tube.

Development:

*Vegetation.*—Strong.

*Blooming.*—Abundant. The productivity is substantially continuous under greenhouse growing conditions and commonly is approximately 120 to 150 blossoms/$m^2$/year.

*Resistance to diseases.*—Very good with a slight sensitivity to Powdery Mildew.

*Formation of hips.*—Hips and seeds sometimes are observed.

I claim:

1. A new and distinct variety of Hybrid Tea rose plant characterized by the following combination of characteristics:

(a) forms in abundance long-lasting attractive blossoms that are light Orient Pink with some light green coloration,
(b) exhibits an erect growth habit,
(c) exhibits blossoms possessing a slight fragrance,
(d) is well suited for cut flower production under greenhouse growing conditions, and
(e) exhibits very good disease resistance;

substantially as herein shown and described.

* * * * *

MB/ACOM